United States Patent [19]

Suh et al.

[11] Patent Number: 4,556,652
[45] Date of Patent: Dec. 3, 1985

[54] ANTIHYPERTENSIVE SPIRO-AMIDOAMINO COMPOUNDS

[75] Inventors: John T. Suh, Greenwich, Conn.; Jerry W. Skiles, Tuckahoe, N.Y.; John J. Piwinski, Parsippany, N.J.; Paul Menard, Tuckahoe; Howard Jones, Ossining, both of N.Y.

[73] Assignee: USV Pharmaceutical Corp., Tarrytown, N.Y.

[21] Appl. No.: 585,769

[22] Filed: Mar. 2, 1984

[51] Int. Cl.[4] .................... A61K 37/00; C07D 279/00; C07C 103/52
[52] U.S. Cl. .................................... 514/211; 514/212; 514/218; 514/222; 544/6; 260/243.3; 260/112.5 R
[58] Field of Search ..................... 260/112.5 R, 243.3; 424/177; 514/211, 212, 218; 544/6

[56] References Cited

FOREIGN PATENT DOCUMENTS 0050800  5/1982  European Pat. Off. ..... 260/112.5 R

Primary Examiner—Delbert R. Phillips

[57] ABSTRACT

Compounds having the general structure

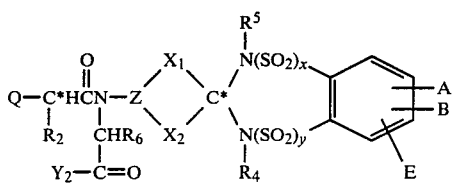

and their pharmaceutically acceptable salts, wherein the substitutents are defined herein, which exhibit antihypertensive activity.

26 Claims, No Drawings

ANTIHYPERTENSIVE SPIRO-AMIDOAMINO COMPOUNDS

BACKGROUND OF THE INVENTION

This application relates to compounds, their pharmaceutically acceptable salts, and pharmaceutical preparations made therefrom, having utility in the treatment of hypertension in subjects suffering therefrom.

SUMMARY OF THE INVENTION

Broadly stated, the present invention comprises compounds of the formula (1)

$$
\begin{array}{c}
\text{R}_5 \\
\text{O} \quad \text{X}_1 \quad | \\
\| \quad / \quad \backslash \quad \text{N(SO}_2)_x \\
\text{Q—C*HCN—Z} \quad \text{C*} \quad \diagdown \quad \text{A} \\
| \quad | \quad \backslash \quad / \quad \diagup \quad \text{B} \\
\text{R}_2 \quad \text{CHR}_6 \quad \text{X}_2 \quad \text{N(SO}_2)_y \\
| \quad | \\
\text{Y}_2\text{—C=O} \quad \text{R}_6 \quad \text{E}
\end{array}
\tag{1}
$$

and their pharmaceutically acceptable acid addition, alkali metal, and alkaline earth metal salts, wherein Q is $Y_1$—C(O)—C*H($R_1$)—NH—, —$NH_2$, $R_1$C(O)—S—C*H($R_1$))$_{0-1}$—, or HS—(C*H($R_1$))$_{0-1}$—;

$Y_1$ and $Y_2$ are independently —OH, —OR, or —$NR_1R_2$;

Z is $$-\overset{/}{\underset{\backslash}{C^*H}} \text{ or } -\overset{/}{\underset{\backslash}{N}} ;$$

one of x and y is 1 and the other is 0;

R is independently hydrogen, alkyl having 1 to 8 carbon atoms, aryl having up to 12 carbon atoms, aryl-alkyl wherein the aryl moiety has up to 10 carbon atoms and the alkyl moiety has 1 to 6 carbon atoms, cycloalkyl having 3 to 10 carbon atoms, fused cycloalkylaryl having 8 to 12 carbon atoms, heterocyclic, or an amino-substituted alkyl having 1 to 6 carbon atoms;

$R_1$ is independently hydrogen, alkyl having 1 to 8 carbon atoms, aryl having up to 12 carbon atoms, aryl-alkyl wherein the aryl moiety has up to 10 carbon atoms and the alkyl moiety has 1 to 6 carbon atoms, cycloalkyl having 3 to 10 carbon atoms, fused cycloalkylaryl having 8 to 12 carbon atoms, heterocyclic, or an amino-substituted alkyl group having 1 to 6 carbon atoms;

$R_2$ is independently hydrogen, alkyl having 1 to 8 carbon atoms, aryl having up to 12 carbon atoms, aryl-alkyl wherein the aryl moiety has up to 10 carbon atoms and the alkyl moiety has 1 to 6 carbon atoms, cycloalkyl having 3 to 10 carbon atoms, fused cycloalkylaryl having 8 to 12 carbon atoms, heterocyclic, or an amino-substituted alkyl group having 1 to 6 carbon atoms;

$R_3$ is —OH, phenyl, or an alkyl or alkoxy group having up to 6 carbon atoms;

$R_4$ and $R_5$ are independently hydrogen, alkyl having 1 to 8 carbon atoms, aryl having up to 12 carbon atoms, aryl-alkyl wherein the aryl moiety has up to 10 carbon atoms and the alkyl moiety has 1 to 6 carbon atoms, cycloalkyl having 3 to 10 carbon atoms, fused cycloalkylaryl having 8 to 12 carbon atoms, heterocyclic, or an amino-substituted alkyl group having 1 to 6 carbon atoms;

$R_6$ is independently hydrogen, alkyl having 1 to 8 carbon atoms, aryl having up to 12 carbon atoms, aryl-alkyl wherein the aryl moiety has up to 10 carbon atoms and the alkyl moiety has 1 to 6 carbon atoms, cycloalkyl having 3 to 10 carbon atoms, fused cycloalkylaryl having 8 to 12 carbon atoms, heterocyclic, or an amino-substituted alkyl group having 1 to 6 carbon atoms;

A, B and E are independently hydrogen, halogen, —OH, —OR, —$CF_3$, —$NR_1R_2$, —C(O)$Y_1$, —$SO_2R$, or —$SO_2NR_1R_2$, provided that at least two of A, B and E are not hydrogen;

$X_1$ is —(CH$_2$)$_a$—, —(CH$_2$)$_b$S(CH$_2$)$_c$—, —(CH$_2$)$_b$N(R)(CH$_2$)$_c$—, —(CH$_2$)$_b$C(O)(CH$_2$)$_c$—, —(CH$_2$)$_b$CH($R_3$)(CH$_2$)$_c$—, $$-(CH_2)_g-C=C-(CH_2)_h-; \quad -(CH_2)_g-C=C-(CH_2)_h-, \text{ or}$$

$$-(CH_2)_g-C=C-(CH_2)_h;$$

(with cyclohexenyl, pyridyl, and pyrrolyl ring structures respectively)

$X_2$ is —(CH$_2$)$_d$—, —(CH$_2$)$_e$S(CH$_2$)$_f$—, —(CH$_2$)$_b$N(R)(CH$_2$)$_c$—, —(CH$_2$)$_e$C(O)(CH$_2$)$_f$—, or —(CH$_2$)$_e$CH($R_3$)(CH$_2$)$_f$—;

provided that a, b, c, d, e, f, g and h are each zero or a positive integer up to 6, and are selected so that the ring formed by $X_1$, $X_2$ and the two atoms to which they are attached contains 5 to 8 atoms; wherein the alkyl, cycloalkyl, aryl, and fused arylcycloalkyl groups may carry substituents selected from the group consisting of alkyl with 1 to 6 carbon atoms, alkoxy with 1 to 6 carbon atoms, —$CF_3$, —OH, —SH, halogen, —$NO_2$, and —COOR.

DETAILED DESCRIPTION OF THE INVENTION

Preferred substituents within the scope of the present invention include those wherein $Y_1$ and $Y_2$ are independently hydroxy, benzyloxy, or alkoxy containing up to 8 carbon atoms;

$R_1$ is H; alkyl having 1 to 8 carbon atoms; phenylalkyl wherein the alkyl has 1 to 4 carbon atoms, and more preferably phenethyl; or indanyl, e.g. 2-indanyl;

$R_2$ is H; alkyl having 1 to 8 carbon atoms; or an alkyl group having 1 to 8 carbon atoms, which is substituted with amino or an amino derivative such as —$NH_2$, —NH—C($NH_2$)=NH or $$-N-C=NCH=CHCH=N;$$
(cyclic structure)

and $R_2$ is more preferably $NH_2(CH_2)_4$—;

$R_6$ is H; alkyl having 1 to 8 carbon atoms; amino-substituted alkyl having 1 to 6 carbon atoms; or phenyl, or phenyl-$C_{1-6}$ alkyl;

A is —$NH_2$; —OH; phenoxy; alkoxy having up to 6 carbon atoms; —$SO_2NR_1R_2$ wherein $R_1$ and $R_2$ are hydrogen or $C_{1-3}$ alkyl, and more preferably both hydrogen;

B is halogen, and more preferably chloro, or —$CF_3$; and E is halogen or hydrogen.

The ring formed by $X_1$, $X_2$, and the atoms to which they are connected, contains a total of 5 to 8 atoms. In a preferred embodiment, Z is

and $X_1$ and $X_2$ are each —$(CH_2)_2$—. $X_1$ or $X_2$ can be substituted with an $R_3$ group which is preferably —OH or alkyl containing 1 to 6 carbon atoms. Preferred substituents for $R_4$ and $R_5$ are —H, or alkyl having 1 to 2 carbon atoms.

The alkyl groups include straight-chained and branched groups, including methyl, ethyl, propyl, isopropyl, butyl, isobutyl, tert-butyl, amyl, iso-amyl, hexyl, and the like. By "halogen" is meant chloro, bromo, iodo, and fluoro.

Preferred substituents for $R_1$, $R_2$ and/or $R_6$ also include cycloalkyl groups, aryl groups, heterocyclic groups, and fused aryl-cycloalkyl groups, as defined herein, any of which can be connected to the main chain of the molecule (1) directly or through an alkylene bridge —$(CH_2)_n$— wherein n is 1 to 6. The preferred cycloalkyl groups include cyclopropyl, cyclobutyl, cyclopentyl, cyclohexyl, cycloheptyl, adamantyl, or norbornyl. The preferred aryl and fused aryl-cycloalkyl groups include phenyl, indolyl, indolino, indanyl, naphthyl, tetrahydronaphthyl, and decahydronaphthyl. Preferred heterocyclic groups include pyridyl, thienyl, furyl, furfuryl, tetrahydrofuryl, quinolyl, isoquinolyl, tetrahydroquinolyl, tetrahydroisoquinolyl, decahydroquinolyl, decahydroisoquinolyl, pyrrolyl, pyrrolidyl, morpholinyl, benzimidazolyl, and imidazolyl. Preferred aryl-alkyl substituents include benzyl and phenethyl. Preferred substituents on the alkyl, cycloalkyl, aryl, and fused aryl-cycloalkyl substituents include alkyl and alkoxy with 1 to 6 carbon atoms, —$CF_3$, —OH, —$NH_2$, phenoxy, —$NR_1R_2$, —COOH, —CN, —SH, halogen, —$NO_2$, and —COOR, preferably COO—($C_{1-6}$ alkyl).

Compounds according to formula (1) can contain asymmetric centers at the carbon atoms marked thus: C*. Each of these carbon atoms can have an (R) or an (S) configuration, and preferably (S). In the preferred compounds the asymmetric spiro carbons are (S) or (R), and the other asymmetric carbons are in the (S) configuration. Individual optical diastereoisomers as well as mixtures thereof are considered to be within the scope of this invention. When diastereoisomeric products result from the synthetic procedures, the desired diastereoisomeric product can be separated by conventional chromatographic or fractional crystallization methods.

The compounds of formula (1) can be prepared by coupling a compound of formula (2)

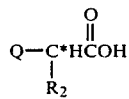

with one of formula (3):

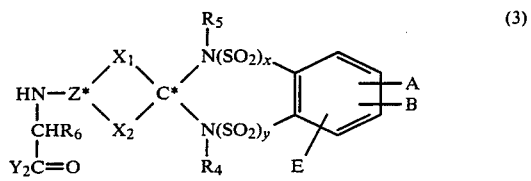

Compound (3) can be prepared by reacting compound (4)

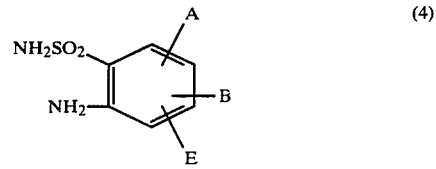

with compound (5)

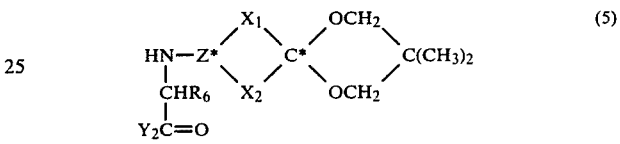

The various substituents on compounds (2), (3) (4), and (5) have the meanings given above.

It will be recognized by those skilled in this art that the coupling of compounds (2) and (3) can be carried out by conventional peptide linkage techniques, e.g. in the presence of a coupling agent such as DCC (N,N'-dicyclohexylcarbodiimide) or CDI (N,N'-carbonyldiimidazole). Alternatively, one may prefer to convert the —COOH group of compound (2) to —C(O)Cl, and then react the resulting intermediate with compound (3). This is the preferred route when Q contains a sulfur atom. Alternatively one may preferably convert the compound (2) to the corresponding N-carboxyanhydride (NCA) by allowing (2) to react with phosgene, and then react the resulting N-carboxyanhydride with compound (3) to yield the desired intermediate. One may alternatively prepare the intermediate spiro amino ester first by reacting compound (2) with compound (5) in any of the above ways (NCA; acid chloride; active ester-peptide coupling) to yield the intermediate which is then reacted with compound (4). It will further be recognized that the nitrogen atom which is between the carbon atoms to which $R_1$ and $R_2$ are attached should be protected with a blocking group such as 2,2,2-trichloroethoxycarbonyl, or benzyloxycarbonyl. The protecting group is subsequently removed, preferably after compounds (2) and (3) have been joined together. Other amine substituents, such as $NH_2(CH_2)_4$—, should be protected and then deprotected in a similar manner. Similarly, $Y_1$ and $Y_2$ are preferably converted to ethoxy, t-butoxy, or benzyloxy, before the intermediates are reacted. If the free acid is desired, it is subsequently obtained by removal of the esterifying group in a known manner.

The compounds of the present invention in which one of $Y_1$ and $Y_2$ is —OH and the other is alkyl, such as methoxy or ethoxy, are preferably made by reacting compounds (2) and (3) as shown above in which one of $Y_1$ and $Y_2$ is the desired alkyl ester, and the other is an easily cleaved ester group such as t-butoxy. The amide thus prepared yields the desired monoester-monoacids upon a mild acid hydrolysis.

The compounds of this invention form salts with various inorganic and organic acids and bases which are also within the scope of the invention. Such salts include ammonium salts, alkali metal salts like sodium and potassium salts (which are preferred), alkaline earth metal salts like the calcium and magnesium salts, salts with organic bases e.g., dicyclohexylamine salts, N-methyl-D-glucamine, salts with amino acids like arginine, lysine and the like. Also, salts with organic and inorganic acids may be prepared, e.g., HCl, HBr, $H_2SO_4$, $H_3PO_4$, as well as methanesulfonic, toluenesulfonic, maleic, acetic, malic, citric, fumaric and camphorsulfonic acids. The non-toxic physiologically acceptable salts are preferred, although other salts are also useful, e.g., in isolating or purifying the product.

The salts may be formed by conventional means, as by reacting the free acid or free base forms of the product with one or more equivalents of the appropriate base or acid in a solvent or medium in which the salt is insoluble, or in a solvent such as water which is then removed in vacuo or by freeze-drying, or by exchanging the cations of an existing salt for another cation on a suitable ion exchange resin.

The action of the enzyme renin on angiotensinogen, a pseudoglobulin in blood plasma, produces the decapeptide angiotensin I. Angiotensin I is converted by angiotensin converting enzyme (ACE) to the octapeptide angiotensin II. The latter is an active pressor substance which has been implicated as the causative agent in various forms of hypertension in various mammalian species, e.g., rats and dogs. The compounds within the scope of this invention which intervene in the renin -to- angiotensin I -to- angiotensin II sequence inhibit angiotensin I converting enzyme and therefore are useful in reducing or relieving hypertension.

Furthermore, the compounds within the scope of the present invention which possess diuretic activity promote relief from hypertension by promoting diuresis, and consequently have utility in treating congestive heart failure. Compounds within the scope of this invention can also simultaneously possess ACE inhibitory and diuretic activity, which is particularly unexpected in view of the fact that such simultaneous activity cannot be predicted from prior art compounds. Thus by the administration of a composition containing one or a combination of compounds of formula (1) or pharmaceutically-acceptable salts thereof, hypertension in the species of mammal suffering therefrom is alleviated. A single dose, or preferably two to four divided daily doses, provided on a basis of about 0.1 to 100 mg per kilogram per day, preferably about 1 to 50 mg per kilogram per day, is appropriate to reduce blood pressure. The substance is preferably administered orally, but a parenteral route such as subcutaneously, intramuscularly, intravenously or intraperitonealy can also be employed.

The compounds of the invention can be utilized to achieve the reduction of blood pressure by formulating one or more of them in compositions such as tablets, capsules or elixirs for oral administration or in sterile solutions or suspensions for parenteral administration. About 10 to 500 mg of a compound or mixture of compounds of formula (1) or physiologically acceptable salt(s) thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule it may contain in addition to materials of the above type a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate, and the like. Buffers, preservatives, antioxidants and the like can be incorporated as required.

EXAMPLE 1

A. Ethyl N-[4-(2,2-dimethyltrimethylene ketal)cyclohexyl]glycinate

To 1,4-cyclohexanedione mono-2,2-dimethyltrimethylene ketal (5.0 g, 0.0240 mole) and glycine ethyl ester hydrochloride (4.52 g, 0.0360 mole) dissolved in absolute ethanol (125 ml) was added sodium cyanoborohydride (1.0 g) portionwise over 45 minutes with external cooling (ice-water bath). The resulting mixture was stirred overnight at room temperature. Ethanol was evaporated and water was added to the residue and then the reaction was basified to pH 8 with concentrated ammonium hydroxide. The product was extracted three times with chloroform, washed with water, dried over magnesium sulfate, filtered and evaporated. The residue was chromatographed over silica-gel using chloroform as the eluent to afford the desired product as a pale yellow oil.

Anal. calc. for $C_{15}H_{27}NO_4$: C, 62.14; H, 9.56; N, 4.83. Found: C, 62.12; H, 9.16; N, 4.23.

B. N-[4-Spiro(6-chloro-3,4-dihydro-7-sulfamoyl-1,2,4-benzothiadiazine-1,1-dioxide)cyclohex-1-yl]glycine ethyl ester hydrochloride Ethyl N-[4-(2,2-dimethyltrimethylene ketal)cyclohexyl]glycinate (6.7 g, 0.0235 mole) and 1-amino-3-chloro-4,6-benzene disulfonamide (2.32 g, 8.15 mmole) were dissolved in ethanol (250 ml) which had been previously saturated with anhydrous hydrogen chloride. The resulting mixture was heated to reflux for three hours. The reaction was cooled to room temperature to afford a solid. Ether was added to the residue and then filtered to afford the desired product as a white solid, M.P. 185° (dec.).

Anal. calc. for $C_{16}H_{23}ClN_4O_6S_2 \cdot HCl.2\frac{1}{2}H_2O$: C, 35.04; H, 5.33; N, 10.22. Found C, 34.55; H, 5.49; N, 9.61.

C.
N-[4-Spiro(6-Chloro-3,4-dihydro-7-sulfamoyl-1,2,4-benzothiadiazine-1,1-dioxide)cyclohex-1-yl]glycine-hydrochloride N-[4-Spiro(6-chloro-3,4-dihydro-7-sulfamoyl-1,2,4-benzothiadiazine-1,1-dioxide)cyclohex-1-yl]-glycine ethyl ester hydrochloride (6.0 g, 11.9 mmol) was added to ethanol (500 ml), then potassium hydroxide (1.34 g, 23.8 mmole) was added. The resulting mixture was stirred overnight at room temperature. Concentrated hydrochloric acid was added dropwise with stirring until pH 3. Water (about 500 ml) was added and the reaction was filtered. The filtrate was evaporated to give a colorless solid. Ether was added to the residue and the solid was filtered and washed with ether to give the product as a colorless solid, m.p. 205°–210°.

Anal. calc. for $C_{14}H_{19}ClN_4O_6S_2 \cdot HCl \cdot H_2O$: C, 34.08; H, 4.50; N, 11.36. Found: C, 34.36; H, 4.58; N, 11.69.

D.
N-[N-[(1S)-1-Ethoxycarbonyl-3-phenylpropyl]-N-(2,2,2-trichloro-ethoxycarbonyl)-L-alanyl]-N-[4-spiro(6-chloro-3,4-dihydro-7-sulfamoyl-1,2,4-benzothiadiazine-1,1-dioxide)cyclohex-1-yl]-glycine ethyl ester To a solution of N-[(1S)-1-ethoxycarbonyl-3-phenylpropyl]-N-(2,2,2-trichloroethoxycarbonyl)-L-alanine (2.76 g, 6.07 mmole) in dry methylene chloride (15 ml) at room temperature under a nitrogen atmosphere was added dropwise oxalyl chloride (1.6 ml) followed by dimethylformamide (12 ul). The resulting solution was stirred for three hours at room temperature. Methylene chloride was evaporated and toluene was added to the residue. The toluene was removed in vacuo (T below 50°) then another portion of toluene was removed in vacuo (T below 50°) and the residue was placed under high vacuum (oil pump) for 30 minutes. The residue was dissolved in dry methylene chloride (7 ml), placed under a nitrogen atmosphere, and cooled to −100° C. To this solution was then added dropwise over a 10 minute period a solution of N-[4-spiro(6-chloro-3,4-dihydro-7-sulfamoyl-1,2,4-benzothiadiazine-1,1-dioxide)cyclohex-1-yl]glycine ethyl ester hydrochloride (3.17 g, 6.22 mmole) and triethylamine (3.80 ml) in dry methylene chloride (28 ml). The mixture was slowly warmed to room temperature and then stirred overnight. Methylene chloride was evaporated and then the residue was dissolved in ethyl acetate. The organic solution was washed twice with 0.1N HCl, twice with water, once with brine, dried over magnesium sulfate, filtered and evaporated to afford the crude product as a pale yellow oil. The crude product was purified by HPLC using as eluent the solvent system of ethyl acetate/n-hexane/ethanol (60:30:5). In this manner the titled compound was separated into two diastereomers having $R_f$ values (silica-gel) of 0.369 and 0.536 in the above solvent system. The compound having an $R_f$ of 0.369 had a melting point of 165°–170° and that with an $R_f$ of 0.536 a melting point of 158°–160°. The major product was that having an $R_f$ of 0.369 (about 9:1).

Anal. calc. for $C_{34}H_{43}Cl_4N_5O_{11}S_2$: C, 45.19; H. 4.80; N, 7.75. Found: C, 45.91; H, 4.90; N, 7.48.

$R_f = 0.369$; m.p. 165°–170°

Anal. calc. for $C_{34}H_{43}Cl_4N_5O_{11}S_2 \cdot C_4H_{10}O$: C, 46.67; H, 5.44. Found: C, 46.69; H, 4.92.

m.p. 158°–160°

E.
N-[N-[(1S)-1-Ethoxycarbonyl-3-phenylpropyl]-L-alanyl]-N-[4-spiro(6-chloro-3,4-dihydro-7-sulfamoyl-1,2,4-benzothiadiazine-1,1-dioxide)cyclohex-1-yl]glycine ethyl ester N-[N-[(1S)-1-Ethoxycarbonyl-3-phenylpropyl]-N-(2,2,2-trichloroethoxycarbonyl)-L-alanyl]-N-[4-spiro(6-chloro-3,4-dihydro-7-sulfamoyl-1,2,4-benzothiadiazine-1,1-dioxide)cyclohex-1-yl]-glycine ethyl ester (0.62 g, 0.686 mmole) was dissolved in glacial acetic acid (6 ml) and then zinc dust (1.8 g) was added portionwise and the resulting mixture was placed under nitrogen. The reaction mixture was stirred at room temperature for 1.5 hours. Zinc was filtered off and washed with a small amount of glacial acetic acid. The filtrate was evaporated in vacuo (T below 45°). Toluene was added to the residue and then evaporated in vacuo (T below 45°). The residue was placed under high vacuum (oil pump) for approximately one hour and then ether was added to the residue to afford the desired product, upon scratching, as a colorless solid which was filtered and washed with ether, m.p. 180°, having the following structure:

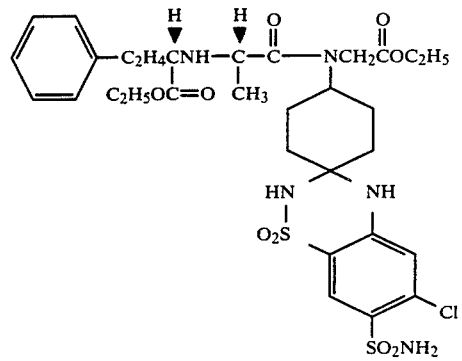

EXAMPLE 2
N-[N-[(1S)-1-Carboxy-3-phenylpropyl]-L-alanyl]-N-[4-spiro(6-chloro-3,4-dihydro-7-sulfamoyl-1,2,4-benzothiadiazine-1,1-dioxide)-cyclohex-1-yl]glycine hydrochloride N-[N-[(1S)-1-Ethoxycarbonyl-3-phenypropyl]-L-alanyl]-N-[4-spiro(6-chloro-3,4-dihydro-7-sulfamoyl-1,2,4-benzothiadiazine-1,1-dioxide)cyclohex-1-yl]glycine ethyl ester (0.50 g, 0.688 mmole) was added to 50 ml of ethanol and placed under nitrogen. Then 1N NaOH (40 ml) was added and the reaction mixture was stirred at room temperature overnight. Most of the ethanol was evaporated in vacuo (T below 45°). Water (about 100 ml) was added to the residue and then concentrated hydrochloric acid was added dropwise with stirring until a pH of approximately 3 was obtained. The product was extracted several times with ethyl acetate, dried over magnesium sulfate, filtered and evaporated to give a solid. Ethanol was added to the residue and the solid product was filtered and washed with ethanol, m.p. 160°.

Anal. calc. for $C_{27}H_{34}ClN_5O_9S_2 \cdot 2HCl \cdot CH_3CH_2OH$: C, 42.08; H, 5.12; N, 8.46. Found: C, 42.09; H, 4.64; N, 8.20.

EXAMPLE 3

A. Nε-Carbobenzoxy-L-lysine ethyl ester

To Nε-carbobenzoxy-L-lysine (69.7 g) was added ethanol (1000 ml) which had been saturated with anhydrous hydrogen chloride. The resulting solution was stirred at room temperature for three days. Ethanol was evaporated in vacuo and the residue was taken up in chloroform (500–600 ml). The chloroform was washed twice with saturated aqueous sodium bicarbonate, filtered and evaporated to afford the desired product as a colorless oil (69.9 g).

B. Nα-[4-(2,2-Dimethyltrimethylene ketal)cyclohex-1-yl]-Nε-carbo-benzoxy-L-lysine ethyl ester Nε-Carbobenzoxy-L-lysine ethyl ester (22 g, 71.3 mmole) and 1,4-cyclohexanedione mono-2,2-dimethyltrimethylene ketal (10.0 g, 50.4 mmole) were dissolved in absolute ethanol (350 ml) in a round bottom flask equipped with a drying tube (Ca SO₄). The reaction was cooled to 5° C. by means of an ice-water bath and then sodium cyanoborohydride (1.99 g) was added portionwise over a thirty minute period. The ice-bath was removed and the reaction was stirred overnight at room temperature. Ethanol was evaporated and water was added to the residue. The product was extracted several times into chloroform, washed once with water, twice with 10% aqueous sodium bicarbonate, again with water, dried over magnesium sulfate, filtered and evaporated to give the crude product. The crude product was purified by HPLC over silica-gel using the solvent system of chloroform-acetone (9:1). In this manner the desired product was obtained as a colorless oil.

Anal. calc. for $C_{27}H_{42}N_2O_6.1 \tfrac{1}{2}H_2O$: C, 62.64; H, 8.76; N, 4.41. Found: C, 62.56; H, 8.48; N, 4.20.

C. Nα-[4-spiro(6-chloro-3,4-dihydro-7-sulfamoyl-1,2,4-benzothiadiazine-1,1-dioxide)cyclohex-1-yl]-Nε-carbobenzoxy-L-lysine ethyl ester Nα-[4-(2,2-dimethyltrimethylene ketal)cyclohex-1-yl]-Nε-carbobenzoxy-L-lysine ethyl ester (4.0 g, 8.15 mmole) and 1-amino-3-chloro-4,6-benzene disulfonamide (2.32 g, 8.15 mmole) were dissolved in ethanol (125 ml) which had been previously saturated with anhydrous hydrogen chloride. The resulting mixture was stirred for three days at room temperature. Ether (about 250 ml) was added to the reaction and the solid was filtered and washed with a small amount of ether. In this manner the desired product, hydrochloride, was obtained as a colorless solid (4.53 g), M.P. 225°–227°.

Anal. calc. for $C_{28}H_{38}ClN_5O_8S_2.1 \tfrac{1}{2}H_2O$: C, 48.09; H, 5.91; N, 10.02. (free base) Found: C, 48.37; H, 5.92; N, 9.40.

D. Nα-[N-[(1S)-1-Ethoxycarbonyl-3-phenylpropyl]-N-(2,2,2-trichloro-ethoxycarbonyl)-L-alanyl]-Nα-[4-spiro(6-chloro-3,6-dihydro-7-sulfamoyl-1,2,4-benzothiadiazine-1,1-dioxide)cyclohex-1-yl]-Nε-carbobenzoxy-L-lysine ethyl ester To a solution of N-[(1S)-1-Ethoxycarbonyl-3-phenylpropyl]-N-(2,2,2-trichloroethoxycarbonyl)-L-alanine (2.0 g, 4.40 mmole) in dry methylene chloride (15 ml) at room temperature under a nitrogen atmosphere was added dropwise oxalyl chloride (1.5 ml) followed by dimethylformamide (12 μL). The resulting solution was stirred for three hours at room temperature. Methylene chloride was evaporated and toluene was added to the residue. The toluene was removed in vacuo (T below 50°) then another portion of toluene was added to the residue. Again the toluene was evaporated in vacuo (T below 50°) and the residue was placed under high vacuum (oil pump) for one hour. The residue was dissolved in dry methylene chloride (10 ml), placed under nitrogen and cooled to 5° C. To this solution was then added dropwise over a 10 minute period a solution of Nα-[4-spiro(6-chloro-3,4-dihydro-7-sulfamoyl-1,2,4-benzothiadiazine-1,1-dioxide)cyclohex-1-yl]-Nε-carbobenzoxy-L-lysine ethyl ester hydrochloride (2.2 g, 3.10 mmole) and triethylamine (2.0 g) in dry methylene chloride (20 ml). The mixture was slowly warmed to room temperature and then stirred overnight. Methylene chloride was evaporated and then the residue was dissolved in ethyl acetate. The organic solution was washed twice with 0.1N HCl, twice with 10% aqueous sodium bicarbonate, twice with water, dried over magnesium sulfate, filtered and evaporated to afford the product as an orange colored glass. Ether was added to the residue causing the above described glass to solidify as an amorphous solid. The solid was filtered and washed with ether to give the desired product as a white solid (2.3 g) m.p. 153°.

Anal calc. for $C_{46}H_{58}Cl_4N_6O_{13}S_2.2 \tfrac{1}{2}H_2O$: C, 47.87; H, 5.50; N, 7.28. Found: C, 47.86; H, 5.13; 7.11.

E. Nα-[N-[(1S)-1-Ethoxycarbonyl-3-phenylpropyl]-N-(2,2,2-trichloro-ethoxycarbonyl)-L-alanyl]-Nα-[4-(2,2-dimethyltrimethylene ketal)cyclohex-1-yl]-Nε-carbobenzoxy-L-lysine ethyl ester To a solution of N-[(1S)-1-ethoxycarbonyl-3-phenylpropyl]-N-(2,2,2-trichloroethoxycarbonyl)-L-alanine (2.76 g, 6.07 mmole) in dry methylene chloride (15 ml) at room temperature under a nitrogen atmosphere was added dropwise oxalyl chloride (1.6 ml) followed by dimethylformamide (12 ul). The resulting solution was stirred for three hours at room temperature. Methylene chloride was evaporated (T below 45°) and toluene was added to the residue. The toluene was removed in vacuo (T below 45°) then another portion of toluene was added to the residue. Again the toluene was evaporated in vacuo (T below 45°) and the residue was placed under high vacuum (oil pump) for one hour. The residue was dissolved in dry methylene chloride (7 ml), placed under a nitrogen atmosphere, and cooled to −10°. To this solution was then added dropwise over a 10 minute period Nα-[4-(2,2-dimethyltrimethylene ketal)cyclohex-1-yl]-Nε-carbobenzoxy-L-lysine ethyl ester (3.09 g, 6.29 mmole) and triethylamine (1.5 ml) in methylene chloride (20 ml). The cooling bath was removed and the reaction was stirred overnight at room temperature. Water was added to the reaction and the product was extracted three times into methylene chloride, washed twice with saturated aqueous sodium bicarbonate, twice with water, dried over magnesium sulfate, filtered and evaporated to give the crude product as a reddish colored oil. The crude product was purified by chromatography over silica-gel using the solvent system of methylene chloride/acetone (95:5) as eluent. The product is reacted with 1-amino-3-chloro-4,6-benzene disulfonamide as in step C. of this example as an alternate route to the product of step D.

F.

Nα-[N-[(1S)-1-Ethoxycarbonyl-3-phenylpropyl]-L-alanyl]-Nα-[4-spiro(6-chloro-3,4-dihydro-7-sulfamoyl-1,2,4-benzothiadiazine-1,1-dioxide)cyclohex-1-yl]-Nε-carbobenzoxy-L-lysine ethyl ester hydrochloride Nα-[N-[(1S)-1-Ethoxycarbonyl-3-phenylpropyl]-N-(2,2,2-trichloroethylcarbonyl)-L-alanyl]-Nα-[4-spiro(6-chloro-3,4-dihydro-7-sulfamoyl-1,2,4-benzothiodiazine-1,1-dioxide)cyclohex-1-yl]-Nε-carbobenzoxy-L-lysine ethyl ester (1.93 g, 1.74 mmole) was dissolved in a mixture of $CH_2Cl_2$/HOAC (20 ml/5 ml respectively) then zinc dust (6.0 g) was added portionwise and the system was placed under a nitrogen atmosphere. The reaction was stirred at room temperature for 2½ hours. The zinc was filtered and washed with a small amount of glacial acetic acid and methylene chloride. Anhydrous hydrogen chloride was bubbled through the filtrate for approximately five minutes. The filtrate was then concentrated in vacuo (T below 45°). Ethyl acetate and water were added to the residue and then concentrated ammonium hydroxide was added dropwise until a pH of 8–9 was obtained. The free base was extracted several times into ethyl acetate. The combined organic extract was washed once with water, dried over magnesium sulfate, filtered and evaporated to give the product as a pale yellow oil (0.71 g).

G.

Nα-[N-[(1S)-Carboxy-3-phenylpropyl]-L-alanyl]-Nα-[4-spiro(6-chloro-3,4-dihydro-7-sulfamoyl-1,2,4-benzothiadiazine-1,1-dioxide)cyclohex-1-yl]-Nε-carbobenzoxy-L-lysine hydrochloride Nα-[N-[(1S)-1-Ethoxycarbonyl-3-phenylpropyl]-L-alanyl]-Nα-[4-spiro(6-chloro-3,4-dihydro-7-sulfamoyl-1,2,4-benzothiadiazine-1,1-dioxide)cyclohex-1-yl]-Nε-carbobenzoxy-L-lysine (0.60 g, 0.644 mmole) was dissolved in ethanol (20 ml) and then 1N NaOH (10 ml) was added. The resulting mixture was stirred overnight at room temperature. Most of the ethanol was evaporated in vacuo (T below 45°). Water was added to the residue followed by the dropwise addition of concentrated hydrochloric acid until a pH of approximately 2 was obtained. The product was extracted several times into ethyl acetate, dried over magnesium sulfate, filtered and evaporated to give the desired product as a colorless solid.

H.

Nα-[N-[(1S)-1-Carboxy-3-phenylpropyl]-L-alanyl]-Nα-[4-spiro(6-chloro-3,4-dihydro-7-sulfamoyl-1,2,4-benzothiadiazine-1,1-dioxide)-cyclohex-1-yl]-L-lysine dihydrobromide Nα-[N-[(1S)-1-Carboxy-3-phenylpropyl]-L-alanyl-Nα-[4-spiro(6-chloro-3,4-dihydro-7-sulfamoyl-1,2,4-benzothiadiazine-1,1-dioxide)cyclohex-1-yl]-Nε-carbobenzoxylysine hydrochloride (0.2 g, 0.228 mmole) was suspended in dry methylene chloride (40 ml) and then twenty-five drops of HBr in acetic acid (40% solution) was added dropwise. The reaction was lightly stoppered and stirred at room temperature for two hours. The reaction was concentrated on a rotary evaporator (T below 45°) and then placed under high vacuum (oil pump) overnight. Ether was added to the residue and the solid which formed was filtered and washed with a small amount of ether. In this fashion the desired dihydrobromide (0.146 g) was obtained as an off-white solid, m.p. 130°–132°.

Anal. calc. for $C_{31}H_{43}ClN_6O_9S_2 \cdot 3HBr$: C, 37.76; H, 4.70. Found: C, 38.11; H, 4.88.

The following compounds are made using the procedures described in Examples 1–3:

EXAMPLE 4

N-[Nα-[(1S)-1-Carboxy-3-phenylpropyl]-L-lysyl]-N-[3-spiro(6-chloro-3,4-dihydro-7-sulfamoyl-1,2,4-benzothiadiazine-1,1-dioxide)-2-methylcyclopent-1-yl]glycine (See formula (1): $Z=CH<$; $X_1=-CH(CH_3)-$; $X_2=-(CH_2)_2-$.

EXAMPLE 5

N-[N-[(1S)-1-Carboxy-3-phenylpropyl]-L-alanyl]-N-[5-spiro(6-chloro-3,4-dihydro-7-sulfamoyl-1,2,4-benzothiadiazine-1,1-dioxide)cyclooct-1-yl]-L-alanine (See formula (1): $Z=-CH<$; $X_1=X_2=-(CH_2)_3-$).

EXAMPLE 6

Nα-[Nα-[(1S)-1-Carboxy-3-phenylpropyl]-L-lysyl]-Nα-[3-spiro(6-chloro-3,4-dihydro-7-sulfamoyl-1,2,4-benzothiadiazine-1,1-dioxide)-thian-5-yl]-L-lysine (See formula (1): $Z=-CH<$; $X_1=-CH_2-$; $X_2=-CH_2SCH_2-$).

EXAMPLE 7

N-[N-[(1S)-1-Carboxy-3-phenylpropyl]-L-alanyl]-N-[3-spiro(6-chloro-3,4-dihydro-7-sulfamoyl-1,2,4-benzothiadiazine-1,1-dioxide)-piperidin-5-yl]glycine (See formula (1): $Z=-CH<$; $X_1=CH_2-$; $X_2=-CH_2NHCH_2-$).

EXAMPLE 8

N-[N-[(1S)-1-Carboxy-3-phenylpropyl]-L-alanyl]-N-[4-spiro(6-chloro-3,4-dihydro-7-sulfamoyl-1,2,4-benzothiadiazine-1,1-dioxide)-piperidin-1-yl]glycine (See formula (1): $Z=-N<$; $X_1=X_2=-(CH_2)_2-$.)

EXAMPLE 9

N-[N-[(1S)-1-Carboxy-3-phenylpropyl]-L-alanyl]-N-[5-spiro(6-chloro-3,4-dihydro-7-sulfamoyl-1,2,4-benzothiadiazine-1,1-dioxide)-3-hydroxy-cyclohex-1-yl]glycine (See formula (1): $Z=-CH<$; $X_1=-CH_2-$; $X_2=-CH_2CHOHCH_2-$).

EXAMPLE 10

N-[Nα-[(1S)-1-Carboxy-3-phenylpropyl]-L-lysyl]-N-[7-spiro(6-chloro-3,4-dihydro-7-sulfamoyl-1,2,4-benzothiadiazine-1,1-dioxide)-5,6,7,8-tetrahydroisoquinolin-5-yl]-L-alanine (See formula (1): $Z=-CH<$;

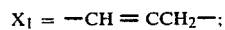

$X_2=-CH_2-$).

EXAMPLE 11

N-[Nα-[(1S)-Carboxy-3-phenylpropyl]-L-lysyl]-N-[3-spiro(6-chloro-3,4-dihydro-7-sulfamoyl-1,2,4-benzothiadiazine-1,1-dioxide)-indan-1-yl]glycine (See formula (1): $Z=-CH$ ;

$X_1 =$ 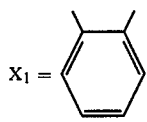

$X_2 = -CH_2-$).

EXAMPLE 12

(S)-N-[3-acetylthio-2-methylpropanoyl]-N-[4-spiro(6-chloro-3,4-dihydro-7-sulfamoyl-1,2,4-benzothiadiazine-1,1-dioxide)cyclohex-1-yl]glycine

EXAMPLE 13

(S)-N-[3-Mercapto-2-methylpropanoyl]-N-[3-spiro(6-chloro-3,4-dihydro-7-sulfamoyl-1,2,4-benzothiadiazine-1,1-dioxide)-indan-1-yl]-L-alanine

EXAMPLE 14

N-[3-(2,2,2-trimethylacetylthio)-2-methylpropanoyl]-[3-spiro(6-chloro-3,4-dihydro-7-sulfamoyl-1,2,4-benzothiadiazine-1,1-dioxide)-cyclopent-1-yl]glycine

EXAMPLE 15

N-[N-[(1S)-1-Ethoxycarbonyl-3-phenylpropyl]-L-alanyl]-N-[4-(6-chloro-3,4-dihydro-7-sulfamoyl-1,2,4-benzothiadiazine-1,1-dioxide)cyclohex-1-yl]glycine

EXAMPLE 16

Nα-[N-[(1S)-1-Ethoxycarbonyl-3-phenypropyl]-L-alanyl]-Nα-[4-(6-chloro-3,4-dihydro-7-sulfamoyl-1,2,4-benzothiadiazine-1,1-dioxide)-cyclohex-1-yl]lysine

EXAMPLE 17

N-[N-[(1S)-Ethoxycarbonyl-3-phenylpropyl]-L-alanyl]-N-[3-spiro(6-chloro-3,4-dihydro-7-sulfamoyl-1,2,4-benzothiadiazine-1,1-dioxide)-indan-2-yl]glycine

What is claimed is:

1. A compound of the formula (1)

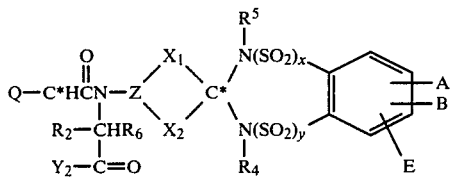

and its pharmaceutically acceptable acid addition, alkali metal, and alkaline earth metal salts, wherein Q is $Y_1-C(O)-C^*H(R_1)-NH-$, $-NH_2$, $R_1-C(O)-S-C^*H(R_1))_{0-1}-$, or $HS-(C^*H(R_1))_{0-1}-$;

$Y_1$ and $Y_2$ are independently $-OH$, $-OR$, or $-NR_1R_2$;

Z is

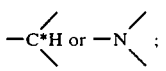

one of x and y is 1 and the other is 0;

R is independently hydrogen, alkyl having 1 to 8 carbon atoms, aryl having up to 12 carbon atoms, aryl-alkyl wherein the aryl moiety has up to 10 carbon atoms and the alkyl moiety has 1 to 6 carbon atoms, cycloalkyl having 3 to 10 carbon atoms, fused cycloalkylaryl having 8 to 12 carbon atoms, heterocyclic, or an amino-substituted alkyl group having 1 to 6 carbon atoms;

$R_1$ is independently hydrogen, alkyl having 1 to 8 carbon atoms, aryl having up to 12 carbon atoms, aryl-alkyl wherein the aryl moiety has up to 10 carbon atoms and the alkyl moiety has 1 to 6 carbon atoms, cycloalkyl having 3 to 10 carbon atoms, fused cycloalkylaryl having 8 to 12 carbon atoms, heterocyclic, or an amino-substituted alkyl group having 1 to 6 carbon atoms;

$R_2$ is independently hydrogen, alkyl having 1 to 8 carbon atoms, aryl having up to 12 carbon atoms, aryl-alkyl wherein the aryl moiety has up to 10 carbon atoms and the alkyl moiety has 1 to 6 carbon atoms, cycloalkyl having 3 to 10 carbon atoms, fused cycloalkylaryl having 8 to 12 carbon atoms, heterocyclic, or an alkyl group having 1 to 6 carbon atoms which is substituted with $-NH_2$, $-NH-C(NH_2)=NH$, or

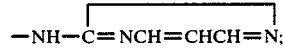

$R_3$ is $-OH$, phenyl, or an alkyl or alkoxy group having up to 6 carbon atoms;

$R_4$ and $R_5$ are independently hydrogen, alkyl having 1 to 8 carbon atoms, aryl having up to 12 carbon atoms, aryl-alkyl wherein the aryl moiety has up to 10 carbon atoms and the alkyl moiety has 1 to 6 carbon atoms, cycloalkyl having 3 to 10 carbon atoms, fused cycloalkylaryl having 8 to 12 carbon atoms, heterocyclic, or an amino-substituted alkyl group having 1 to 6 carbon atoms;

$R_6$ is independently hydrogen, alkyl having 1 to 8 carbon atoms, aryl having up to 12 carbon atoms, aryl-alkyl wherein the aryl moiety has up to 10 carbon atoms and the alkyl moiety has 1 to 6 carbon atoms, cycloalkyl having 3 to 10 carbon atoms, fused cycloalkylaryl having 8 to 12 carbon atoms heterocylic, or an amino-substituted alkyl group having 1 to 6 carbon atoms;

A, B and E are independently hydrogen, halogen, $-OH$, $-OR$, $-CF_3$, $-NR_1R_2$, $-C(O)Y_1$, $-SO_2R$, $-SO_2NR_1R_2$ provided that at least two of A, B and E are not hydrogen;

$X_1$ is $-(CH_2)_a-$, $-(CH_2)_bS(CH_2)_c-$, $-(CH_2)_bN(R)(CH_2)_e-$, $-(CH_2)_bC(O)(CH_2)_c-$, $-(CH_2)_bCH(R_3)(CH_2)_c-$;

 

$-(CH_2)_gC=C-(CH_2)_h-$, $-(CH_2)_gC=C-(CH_2)_h-$, or

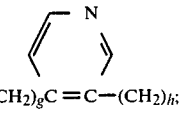

$-(CH_2)_gC=C-(CH_2)_h$;

$X_2$ is $-(CH_2)_d-$, $-(CH_2)_eS(CH_2)_f-$, $-(CH_2)_bN(R)(CH_2)_e-$, $-(CH_2)_eC(O)(CH_2)_f-$, or $-(CH_2)_eCH(R_3)(CH_2)_f-$;

provided that a, b, c, d, e, f, g, and h are each zero or a positive integer up to 6, and are selected so that the ring formed by $X_1$, and $X_2$, and the two atoms to which they are attached contains 5 to 8 atoms; wherein the alkyl, cycloalkyl, aryl, and fused aryl-cycloalkyl groups may carry substituents selected from the group consisting of alkyl with 1 to 6 carbon atoms, alkoxy with 1 to 6 carbon atoms, —$CF_3$, —OH, —SH, halogen, —$NO_2$, and —COOR.

2. A compound or salt according to claim 1 wherein each asymmetrical spiro carbon atom is in the (S) or (R) configuration and the other unsymmetrical carbon atoms are in the (S) configuration.

3. A compound or salt according to claim 1 wherein E, $R_4$ and $R_5$ are hydrogen, and Z is —C*H—.

4. A compound or salt according to claim 3 wherein $X_1$ is —$(CH_2)_a$— and $X_2$ is —$(CH_2)_d$.

5. The compound and salts thereof according to claim 1 which is N-[N-(1S)-1-Ethoxycarbonyl-3-phenylpropyl]-L-alanyl]-N-[4-spiro(6-chloro-3,4-dihydro-7-sulfamoyl-1,2,4-benzothiadiazine-1,1-dioxide)cyclohex-1-yl]glycine ethyl ester.

6. The compound and salts thereof according to claim 1 which is N-[N-[(1S)-1-Carboxy-3-phenylpropyl]-L-alanyl]-N-[4-spiro(6-chloro-3,4-dihydro-7-sulfamoyl-1,2,4-benzothiadiazine-1,1-dioxide)-cyclohex-1-yl]glycine hydrochloride.

7. The compound and salts thereof according to claim 1 which is Nα-[(1S)-1-Carboxy-3-phenylpropyl]-L-alanyl]-Nα-spiro(6-chloro-3,4-dihydro-7-sulfamoyl-1,2,4-benzothiadiazine-1,1-dioxide)-cyclohex-1-yl-L-lysine dihydrobromide.

8. A pharmaceutical preparation comprising an antihypertensive effective amount of a compound or salt according to claim 1 in association with a pharmaceutically acceptable carrier.

9. The method of alleviating hypertension in a host suffering therefrom which comprises administering to said host a therapeutically effective amount of a compound or salt according to claim 1.

10. The compound and salts thereof according to claim 1 which is Nα-[N-[(1S)-1-ethoxycarbonyl-3-phenylpropyl]-L-alanyl]-Nα-[4-spiro(6-chloro-3,4-dihydro-7-sulfamoyl-1,2,4-benzothiadiazine-1,1-dioxide)cyclohex-1-yl]-Nε-carbobenzoxylysine ethyl ester hydrochloride.

11. The compound and salts thereof according to claim 1 which is Nα-[N-[(1S)-1-carboxy-3-phenylpropyl]-L-alanyl]-Nα-[4-spiro(6-chloro-3,4-dihydro-7-sulfamoyl-1,2,4-benzothiadiazine-1,1-dioxide)cyclohex-1-yl]-Nε-carbobenzoxylysine hydrochloride.

12. The compound and salts thereof according to claim 1 which is Nα-[N-[(1S)-1-carboxy-3-phenylpropyl]-L-lysyl]-N-[3-spiro(6-chloro-3,4-dihydro-7-sulfamoyl-1,2,4-benzothiadiazine-1,1-dioxide)-2-methylcyclopent-1-yl]glycine.

13. The compound and salts thereof according to claim 1 which is N-[N-[(1S)-1-carboxy-3-phenylpropyl]-L-alanyl]-N-[5-spiro(6-chloro-3,4-dihydro-7-sulfamoyl-1,2,4-benzothiadiazine-1,1-dioxide)cyclooct-1-yl]-L-alanine.

14. The compound and salts thereof according to claim 1 which is Nα-[Nα-[(1S)-1-carboxy-3-phenylpropyl]-L-lysyl-Nα-[3-spiro(6-chloro-3,4-dihydro-7-sulfamoyl-1,2,4-benzothiadiazine-1,1-dioxide)-thian-5-yl]-L-lysine.

15. The compound and salts thereof according to claim 1 which is N-[N-[(1S)-1-carboxy-3-phenylpropyl]-L-alanyl]-N-[3-spiro(6-chloro-3,4-dihydro-7-sulfamoyl-1,2,4-benzotiadiazine-1,1-dioxide)-piperidin-5-yl]glycine.

16. The compound and salts thereof according to claim 1 which is N-[N-[(1S)-1-carboxy-3-phenylpropyl]-L-alanyl]-N-[4-spiro(6-chloro-3,4-dihydro-7-sulfamoyl-1,2,4-benzothiadiazine-1,1-dioxide)-piperidin-1-yl]glycine.

17. The compound and salts thereof according to claim 1 which is N-[N-[(1S)-1-carboxy-3-phenylpropyl]-L-alanyl]-N-[5-spiro(6-chloro-3,4-dihydro-7-sulfamoyl-1,2,4-benzothiadiazine-1,1-dioxide)-3-hydroxy-cyclohex-1-yl]glycine.

18. The compound and salts thereof according to claim 1 which is N-[Nα-[(1S)-1-carboxy-3-phenylpropyl]-L-lysyl]-N-[7-spiro(6-chloro-3,4-dihydro-7-sulfamoyl-1,2,4-benzothiadiazine-1,1-dioxide)-5,6,7,8-tetrahydroisoquinolin-5-yl]-L-alanine.

19. The compound and salts thereof according to claim 1 which is N-[Nα-[(1S)-1-carboxy-3-phenylpropyl]-L-lysyl]-N-[3-spiro(6-chloro-3,4-dihydro-7-sulfamoyl-1,2,4-benzothiadiazine-1,1-dioxide)-indan-1-yl]glycine.

20. The compound and salts thereof according to claim 1 which is (S)-N-[3-acetylthio-2-methylpropanoyl]-N-[4-spiro(6-chloro-3,4-dihydro-7-sulfamoyl-1,2,4-benzothiadiazine-1,1-dioxide)cyclohex-1-yl]glycine.

21. The compound and salts thereof according to claim 1 which is (S)-N-[3-mercapto-2-methylpropanoyl]-N-[3-spiro(6-chloro-3,4-dihydro-7-sulfamoyl-1,2,4-benzothiadiazine-1,1-dioxide)-indan-1-yl]-L-alanine.

22. The compound and salts thereof according to claim 1 which is N-[3(2,2,2-trimethylacetylthio)-2-methylpropanoyl]-3-spiro(6-chloro-3,4-dihydro-7-sulfamoyl-1,2,4-benzothiadiazine-1,1-dioxide)-cyclopent-1-yl]glycine.

23. the compound and salts thereof according to claim 1 which is -N-[N-[(1S)-1-ethoxycarbonyl-3-phenylpropyl]-L-alanyl]-N-[4-(6-chloro-3,4-dihydro-7-sulfamoyl-1,2,4-benzothiadiazine-1,1-dioxide)cyclohex-1-yl]glycine.

24. The compound and salts thereof according to claim 1 which is Nα-[N-[(1S)-1-ethoxycarbonyl-3-phenylpropyl]-L-alanyl]-Nα-[4-(6-chloro-3,4-dihydro-7-sulfamoyl-1,2,4-benzothiadiazine-1,1-dioxide)cyclohex-1-yl]lysine.

25. The compound and salts thereof according to claim 1 which is N-[N-[(1S)-1-ethoxycarbonyl-3-phenylpropyl]-L-alanyl]-N-[3-spiro(6-chloro-3,4-dihydro-7-sulfamoyl-1,2,4-benzothiadiazine-1,1-dioxide)-indan-2-1-yl]glycine.

26. The compound and salts thereof according to claim 1 which is (S)-N-[3-mercapto-2-methylpropanoyl]-N-[4-spiro(6-chloro-3,4-dihydro-7-sulfamoyl-1,2,4-benzothiadiazine-1,1-dioxide)cyclohex-1-yl)glycine.

* * * * *